(12) United States Patent
Huang et al.

(10) Patent No.: US 7,138,150 B2
(45) Date of Patent: Nov. 21, 2006

(54) METHOD OF MAKING AN ANTI-INFECTIVE COMPOSITION FOR TREATING ORAL INFECTIONS

(75) Inventors: Ning Huang, Davis, CA (US); Jianmin Huang, Davis, CA (US); Delia R. Bethell, Sacramento, CA (US)

(73) Assignee: Ventria Bioscience, Sacramento, CA (US)

( * ) Notice: Subject to any disclaimer, the term of this patent is extended or adjusted under 35 U.S.C. 154(b) by 706 days.

(21) Appl. No.: 10/639,781

(22) Filed: Aug. 13, 2003

(65) Prior Publication Data

US 2004/0063617 A1    Apr. 1, 2004

Related U.S. Application Data

(63) Continuation-in-part of application No. 10/077,381, filed on Feb. 14, 2002, now Pat. No. 6,991,824, and a continuation-in-part of application No. 09/847,232, filed on May 2, 2001, now abandoned.

(60) Provisional application No. 60/269,199, filed on Feb. 14, 2001, provisional application No. 60/266,929, filed on Feb. 6, 2001, provisional application No. 60/201,182, filed on May 2, 2000.

(51) Int. Cl.
*A61K 9/68* (2006.01)
*A61K 9/20* (2006.01)
*C12N 15/12* (2006.01)

(52) U.S. Cl. ................ 426/3; 424/94.63; 424/440; 424/464

(58) Field of Classification Search ............... 800/288, 800/320, 320.2, 317.3, 317.4; 424/94.63, 424/535, 750, 776, 440, 464; 426/3, 656
See application file for complete search history.

(56) References Cited

U.S. PATENT DOCUMENTS

| | | | |
|---|---|---|---|
| 5,571,896 | A | 11/1996 | Conneely et al. |
| 5,585,257 | A | 12/1996 | De Baetselier et al. |
| 5,618,712 | A | 4/1997 | Sledziewski et al. |
| 5,955,316 | A | 9/1999 | Conneely et al. |
| 6,066,469 | A | 5/2000 | Kruzel et al. |
| 6,319,895 | B1 | 11/2001 | Tomita et al. |
| 6,455,687 | B1 | 9/2002 | Kruzel et al. |
| 6,528,297 | B1 | 3/2003 | Yu et al. |
| 6,569,831 | B1 | 5/2003 | Legrand et al. |
| 2003/0074700 | A1 | 4/2003 | Huang et al. |

FOREIGN PATENT DOCUMENTS

WO        00/04146    *   1/2000

* cited by examiner

*Primary Examiner*—Keith Hendricks
(74) *Attorney, Agent, or Firm*—Arent Fox PLLC

(57) ABSTRACT

This invention concerns a method of making an anti-infective composition for oral administration using an agent selected from the group consisting of lactoferrin protein and lysozyme protein. The method comprises three steps. The nucleic acid, which encodes a lactoferrin or lysozyme protein, is expressed in a monocot seed. The protein is isolated from the seed. This protein isolation compromises greater than 3% of the total soluble protein in the monocot seed. The protein is then formulated for oral administration.

11 Claims, No Drawings

METHOD OF MAKING AN ANTI-INFECTIVE COMPOSITION FOR TREATING ORAL INFECTIONS

This application is a continuation in part of U.S. patent application Ser. No. 10/077,381 filed Feb. 14, 2002, now U.S. Pat. No. 6,991,824, which is incorporated by reference in its entirety herein. Accordingly, the application also claims priority benefit to U.S. provisional application Ser. No. 60/269,199, filed Feb. 14, 2001, for "Expression of Human Milk Proteins in Transgenic Plants", which is incorporated herein in its entirety. That application is also a continuation-in-part of U.S. patent application Ser. No. 09/847,232, filed May 2, 2001, for "Plant Transcription Factors and Enhanced Gene Expression", now abandoned, which claims the benefit of U.S. provisional application Ser. No. 60/266,929, filed Feb. 6, 2001, and U.S. provisional application Ser. No. 60/201,182, filed May 2, 2000, all of which are incorporated herein by reference. The corresponding PCT application No. PCT/US01/14234, International Publication No. WO 01/83792 A1, published Nov. 8, 2001, is also incorporated herein by reference in its entirety.

FIELD OF THE INVENTION

The present invention relates to a method of making an oral, anti-infective composition for treating oral infections. The lactoferrin and lysozyme proteins, which are the active ingredients of the anti-infective compound, are recombinantly produced in the seeds of monocot plants.

BACKGROUND OF THE INVENTION

Human Lactoferrin is an iron-binding single chain polypeptide of 692 amino acids organized into two globular lobes, representing its N-terminal and C-terminal. Each lobe is itself folded into two domains (N-lobe: N1 and N2; C-lobe: C1 and C2) that enclose the iron binding sites. This two-lobe, four-domain structure provides the key to understanding the dynamic properties of lactoferrin. Lactoferrin undergoes a conformational change as iron is bound (closed form) or released (open form). Lactoferrin is a multifunctional glycoprotein produced and secreted by acinar epithelial cells and neutraphils. It is a member of the transferring family of iron binding proteins, but it is also reported to have anti-microbial, antioxidant and immunomodulatory activities. The mature lactoferrin (LF) polypeptide is relatively resistant to proteolysis, is glycosylated at two sites (N138 and N478) and has a molecular weight of about 80 kD.

Lactoferrin is found in the granules of neutrophils where it apparently exerts an anti-microbial activity by withholding iron from ingested bacteria and fungi; it also occurs in many secretions and exudates (milk, tears, mucus, saliva, bile, etc.). In addition to its role in iron transport, lactoferrin has bacteriostatic and bactericidal activities, in addition to playing a role as an antioxidant.

Human milk lysozyme, called muramidase or peptidoglycan N-acetylmuramoyl-hydrolase (EC 3.2.1.17) contains 130 amino acid residues and is a protein of 14.7 kDa in size. Human lysozyme is non-glycosylated and possesses unusual stability in vitro and in vivo due to its amino acid and secondary structure. Lysozymes act as enzymes that cleave peptidoglycans, and ubiquitous cell wall component of microorganisms, in particular bacteria. Specifically, lysozymes are 1,4-β-acetylmuramidases that hydrolyze the glycoside bond between N-acetylmuramic acid and N-acetylglucosamine. Gram-positive bacteria are highly susceptible to lysozyme due to the polypeptidoglycan on the outside of the cell wall. Gram-negative strains have a single polypeptidoglycan layer covered by lipopolysaccharides and are therefore less susceptible to lysis by lysozyme, however, the sensitivity can be increased by the addition of EDTA (Schüitte, H. and Kula, M. R. (1990) *Biotechnol. Appl. Biochem.* 12: 599–620).

Lactoferrin and lysozyme are found in saliva of healthy individuals, along with IgA, histatins and other natural defense proteins. Saliva flow and anti-microbial proteins appear to function together to maintain oral health by cleansing the mouth of debris and action of oral host defense proteins. The two proteins lactoferrin and lysozyme have anti-fungal activity individually and in combination and their combined action can be synergistic.

Human lactoferrin binds a specific receptor in Caco-2 cells for transport across the membrane. Bovine lactoferrin does not bind this receptor. Human lysozyme has significantly greater lytic activity than the commonly used chicken egg white lysozyme.

*Candida albicans* is a component found in the mouth of many healthy people. However, oral candidiasis caused by this and related organisms, is one of the most common opportunistic infections of the oral cavity. Oropharyngeal candidiasis (OPC) is a frequent infection in immunocompromised individuals, particularly HIV/AIDS and cancer patients. It is also found associated with steroid drug therapy, diabetes, high carbohydrate diet and other immunosuppressive conditions. The tongue and buccal mucosa lesions, although not considered life threatening, can be extremely uncomfortable and result in decrease food and liquid intake as well as reduced compliance in taking medications. Failure to treat or resolve the oral infection can lead to spread of the infection to the esophagus and ultimately to disseminated candidiasis.

In addition to the difficulties of candidiasis itself, a number of recent reports have dealt with development of resistance to the azoles in patients treated for oropharyngeal candidiasis (OPC). This resistance appears to develop in both chronically and intermittently treated patients. Resistance is more common in immunosupressed patients than otherwise healthy patients. The development of resistance may manifest itself by treatment failure due to replacement of *C. albicans* with a strain more inherently resistant, such as *C. dubliniensis* or the development of resistance in *C. albicans* itself. The infection can be controlled in many resistant strains by increasing the dosage of the azole compounds; however, this can lead to increased toxicity and side effects. The institution of HAART (highly active antiretroviral treatment) has reduced the frequency of oral *Candida albicans* infections in HIV and AIDS patients, however, it is not clear whether this is due to the action of the protease inhibitors on aspartic proteinase or the improvement in the immune system with the increase in the number of CD4+T cells. There are also anecdotal reports of recurrent OPC during HAART.

Conventional technology has disclosed methods of producing anti-microbial and anti-fungal protein agents in recombinant hosts, such as monocotyledon plants. These methods, however, produce low quantities of resulting protein product, thereby making these methods inefficient and potentially costly in an economic sense.

U.S. Pat. No. 6,569,831 to Legrand et al ("Legrand") discloses methods of production of recombinant protein, such as lactoferrin, from plants. Legrand teaches the use of lactoferrin, proteins as anti-microbial agents and anti-fungal agents, particularly against *Candida*. The method includes transforming a monocot plant cell with a recombinant vector, which comprises a nucleic acid molecule encoding for lactoferrin. Legrand teaches the use of a genetically transformed plant, chosen from amongst rape, tobacco, maize, peas, tomatoes, carrots, wheat, barley, potatoes, soy, sunflower, lettuce, rice, alfalfa, and beets. These genetically transformed plants are manipulated to produce lactoferrin. Legrand teaches the use of several promoters in its recombinant technology. These include 35S (P35S), Pd35S of the CaMV, PCRU of the radish cruciferin, PGA1 and PGA6 of *Arabidopsis thalianai*, PSP from *Agrobacterium tumefaciens*, rice actin promoter followed by the actin intron, barley HMWG, and maize γzein gene promoter (Pγzein).

The protein is then expressed in the plant cell and isolated. According to Legrand, the ratio of recombinant human lactoferrin varies by the selection of transformant. According to the methods disclosed in this reference, however, the percent ratio of recombinant human lactoferrin to total soluble proteins in monocot leaves reached 0.1% in the best case. Immunodetection in maize seed was also observed, but no quantities of expression were provided.

The method disclosed in Legrand to produce lactoferrin using genetically transformed monocots provides a general framework for recombinant human protein production in plants. However, Legrand does not disclose a method that produces a relatively high-yield of protein product. For instance, Legrand does not teach a method that can produce protein products greater than 3% of the total soluble protein in the monocot seed.

It would be advantageous to provide a safe, affordable, recombinantly produced anti-fungal agent for treating oral infections in immuno-compromised patients and others. It would also be advantageous to have a method of producing an anti-infective protein agent using recombinant technology in monocots that results in a relatively high yield of the protein product.

SUMMARY OF THE INVENTION

The invention includes a method of making an anti-infective composition suitable for oral administration comprising an agent including at least one protein selected from the group consisting of lactoferrin protein and lysozyme protein, comprising the steps of:

expressing a nucleic acid encoding at least one protein selected from the group consisting of lactoferrin protein and lysozyme protein or portion thereof in a monocot seed;

isolating the at least one protein from the seed, wherein the at least one protein comprises about 3% or greater of the total soluble protein in the seed;

combining the at least one protein with a pharmaceutically acceptable carrier or diluent to provide a composition suitable for oral administration.

Additional advantages and novel features of the invention will be set forth in part in the description that follows, and in part will become more apparent to those skilled in the art upon examination of the following or upon learning by practice of the invention.

DETAILED DESCRIPTION OF THE INVENTION

Unless otherwise indicated, all terms are generally consistent with same meaning that the terms have to those skilled in the art of the present invention. Practitioners are particularly directed to Sambrook et al. (1989) Molecular Cloning: A Laboratory Manual (Second Edition), Cold Spring Harbor Press, Plainview, N.Y. and Ausubel F M et al. (1993) Current Protocols in Molecular Biology, John Wiley & Sons, New York, N.Y., for definitions and terms of the art. It is to be understood that this invention is not limited to the particular methodology, protocols, and reagents described, as these may vary.

Terms defined and specified in U.S. Ser. No. 10/077,381 filed on Feb. 14, 2002, and WO 01/83792 A1, published Nov. 8, 2001, both of which are incorporated herein by reference in their entirety, are specifically incorporated by reference in this application.

The invention provides protein agents (lactoferrin and lysozyme) recombinantly produced in host monocot plant seed wherein the protein expressed comprises about 3% or greater of the total soluble protein in the monocot seed. Thus, for example, the yield of total soluble protein which comprises the lactoferrin or lysozyme protein targeted for production can be from about 3% to about 5%, from about 5% to about 10%, from about 10% to about 15%, from about 15% to about 20%, from about 20% to about 25%, and from about 25% to about 30% of the total soluble protein found in the recombinantly engineered production plant seed. Additionally, for example, the yield of total soluble protein which comprises the lactoferrin or lysozyme protein targeted for production can be about 3% or greater, about 5% or greater, about 10% or greater, about 15% or greater, about 20% or greater, and about 25% or greater. Such optimization of a recombinant protein production system vastly improves not only the yields of usable protein for use as agents in an oral anti-infective composition, but also provides the opportunity for making an oral formulation having optimal concentrations of active agent to effectively combat an oral infection upon administration to infected individuals.

The present invention provides a method of producing recombinant human lactoferrin and human lysozyme for administration to persons in need of protection or treatment for an oral infection, particularly oral candidiasis. Lactoferrin and lysozyme are provided from recombinant production in monocot seeds using a recombinant production system that optimizes the yield of recombinant protein to preferably greater than 3% of the total soluble protein extractable from the mature seed of the monocot plant.

For recombinant production of the proteins, the techniques described in co-pending application U.S. Ser. No. 10/077,381, filed Feb. 14, 2002, provide extensive details on recombinant production of human lactoferrin and human lysozyme in monocot plants and examples illustrating the process and results of such production for human lactoferrin and lysozyme proteins. Thus, lactoferrin and lysozyme proteins produced in plants can be produced in the seeds or grains of transgenic monocot plants expressing the nucleic acid coding sequence for the desired protein. Following expression, recombinant protein is isolated from these host transgenic grains.

In brief, production of plant-produced recombinant lactoferrin or lysozyme can be based on the expression of recombinant human lactoferrin (rhLF) and recombinant human lysozyme (rhLY) under the control of a seed specific promoter in rice. The recombinant proteins produced in these plants under the described system may be glycosylated, preferably containing one or more plant glycosylation groups. The human protein produced by transgenic plants is compared to the native human protein form for rhLF and rhLY and information on the stability of the recombinant protein and the advantages of using rice grain containing such recombinant human lactoferrin protein is further described in U.S. Ser. No. 10/077,381.

The invention relies on the use of heterologous nucleic acid constructs including the coding sequence for lactoferrin or lactoferrin polypeptide and for lysozyme or lysozyme polypeptide of therapeutic value, exemplified in U.S. Ser. No. 10/077,381 and PCT Application No. PCT/US01/14234. Expression vectors for generation of transgenic plants expressing human lactoferrin protein are described in U.S. Ser. No. 10/077,381 and PCT Application No. PCT/US01/14234. Exemplary methods for constructing chimeric genes and transformation vectors carrying the chimeric genes are given in U.S. Ser. No. 10/077,381 including promoters, signal and transport sequences, protein coding sequences, variant human lactoferrin protein-encoding nucleic acid sequences, and variant human lysozyme protein-encoding nucleic acid sequences, codon optimization for both proteins, transcription factor coding sequences, additional expression vector components, the generation of transgenic plants, the plant hosts, and detecting expression of recombinant human lactoferrin protein and recombinant human lysozyme protein.

For example, a heterologous nucleic acid construct or expression vector designed for operation in plants, may include (i) a promoter (transcriptional regulatory region) induced in particular seed tissue ("seed specific"); (ii) the coding sequence for a plant transcription factor operably linked to the promoter; (iii) companion sequences upstream and downstream which are of plasmid or viral origin and provide necessary characteristics to the vector to permit the vector to move the DNA from bacteria to the desired plant host; (iv) a selectable marker sequence; and (v) a transcriptional termination region generally at the opposite end of the vector from the transcription initiation regulatory region. Vector components may also include a signal sequence. The transcription regulatory and promoter region of the chimeric gene or heterologous nucleic acid construct is preferably a seed-specific promoter. Moreover, expression vectors or heterologous nucleic acid constructs, designed for operation in plants, comprise companion sequences upstream and downstream from the expression cassette. The companion sequences are of plasmid or viral origin and provide necessary characteristics to the vector to permit the vector to move DNA from bacteria to the plant host. Further description of constructs is presented in WO/01/83792, which is incorporated in its entirety herein.

Isolation of the recombinant protein is also described in U.S. Ser. No. 10/077,381. Yields of recombinant protein produced in monocot seeds by the system disclosed and described herein and in the parent application U.S. Ser. No. 10/077,381 exceed 3% of the total soluble protein, and in some cases can be as great as 30% of the total soluble protein in the host seed. Such high yields (above 3% of total soluble protein) optimize the use of plant produced rhLF and rhLY in monocots for the intended purpose as an oral anti-infective.

Methods for purifying recombinant lactoferrin and lysozyme are known to those skilled in the art. For example, purification methods include extraction, filtration and diafiltration, washing, and chromatography. Examples of the chromatography methods include affinity chromatography to BrCN activated 4B Sepharose gel, ion exchange chromatography (both anioic and cationic) with SP Sepharose Fast Flow column resins, control pore glass chromatography, and T-Gel chromatography, IEF chromatography and HPLC chromatography. For additional descriptions of purification procedures, see U.S. Pat. No. 5,571,896, U.S. Pat. No. 6,569,831, U.S. Pat. No. 6,455,687, U.S. Ser. No. 10/077,381, and WO 01/83792 A1, which are incorporated herein by this reference.

In mild to moderate cases of Oropharyngeal candidiasis (OPC), the first line of defense is topical oral formulations. Examples of such forms include a chewing-gum form, a chewable form including chewable tablets, lozenges, mucoadhesive film (dissolving film), dental paints, viscous gels, dental implants, polymer film adhesives, a troche form, syrups or elixirs, a toothpaste form, a gargling-gel form, mouth-rinse form, a suspension form, and other similar forms. Exemplary methods for using forms for oral administration are described in U.S. Pat. Nos. 6,379,651, 6,479,051, 6,592,887, 5,846,971, 6,066,469, and 5,116,603, which are incorporated herein in their entirety. The invention contemplates formulation of lactoferrin alone, lysozyme alone, or lactoferrin and lysozyme together in suitable oral formulation. In general any formulation that provides contact of the active agent with the infected site in the mouth will suit for delivery of the lactoferrin and lysozyme. Lozenges can be more effective than mouth rinses since they can prolong contact with the active ingredient while the patient retains the lozenge in the mouth. Suspensions are swallowed and act through topical and systemic mechanisms. Topical treatment options include polyene agents (nystatin and amphotericin B) and azoles (clotrimazole, ketoconazole, fluconazole and itraconazole). The invention provides, in one embodiment, a composition formulated in a lozenge for placement in the mouth where it can dissolve and act on the infected regions within the mouth.

In determining the amount of grain, extract, or malt material to be used in the composition, it is useful to determine the amount of any lactoferrin protein or lysozyme protein present and add an amount of pharmaceutically compatible materials, such as excipients or diluents, bringing the final level of lactoferrin protein and lysozyme protein to a desired level per dosage amount in the composition. U.S. Ser. No. 10/077,381 describes different compositions possible from plant-produced recombinant human lactoferrin, e.g. including flour composition, extract composition, malt composition, and including also various other processes of extraction of recombinant protein from plant seeds. Any of these compositions or combinations thereof can be used in formulating an oral formulation.

In particular, the invention contemplates formulation of the active ingredient or ingredients into a lozenge. Lozenges are solid or semi-solid delivery systems that are intended to dissolve or disintegrate slowly in the mouth. Typically, they contain drugs that are intended primarily for local effect on the buccal lining. Antibacterial and antifungal agents are ideal candidates for incorporation into lozenges to treat oral candidiasis.

Lozenges can be formulated by one of the following three techniques: hot molding, warm molding or compression. Hot molding involves the use of high concentration of sugars and high temperature (usually higher than 80° C.) and is therefore typically unsuitable for protein-based active ingredients. For the purpose of delivering rhLF and rhLY, the methods of warm molding and compression are preferably used to obtain several feasibility formulations. These are tested for the drug release profile and dissolution profile in accordance with known products.

Warm-molding formed lozenges are based either on use of a slow dissolving polymer such as polyethylene glycol (PEG) or a sugar-starch gum base. Since the active ingredients in the present formulations are intended to treat organisms that can use sugars to grow, the lozenge is preferably formed of a polyethylene glycol base. An exemplary method which can be used is as follows: PEG 1000 or 1450 is warmed to a temperature of about 40–50° C. to make it soft. The recombinant proteins, dissolved in a small amount of water or glycerin are mixed with the mass to obtain a uniform solution/suspension. A suitable sweetener (such as for example, sucrose, fructose, or aspartame) is added to the preparation along with a flavor and color (for example, peppermint or lemon). The preparation is poured into suitable size molds maintained at 40–50° C. and allowed to cool to room temperature. The temperature is adjusted to a point to allow partial congealing of material before pouring to prevent settling of materials during cooling.

A typical formula is as follows:

| | |
|---|---|
| Actives Ingredients | 0.25–5 g |
| PEG 1000 | 90 g |
| Aspartame | 0.5 g |
| Peppermint oil | 0.1 mL |
| Color | As needed |

Compression-formed lozenges offer greater flexibility in formulation variables and yield a solid product. The force of compression can be used as one of the variables to control the rate of dissolution of the lozenges. A typical method involves mixing the actives with a solid carrier such as soluble starch (e.g. partially hydrolyzed starch), sugar or sugar free sweeteners, and other ingredients such as lubricants and diluents to make up the appropriate size of the formulation. The mixture can be compressed to a breaking strength of about 20 kg force. These compressed tablets do not disintegrate but tend to slowly dissolve in saliva. Appropriate ingredients such as organic acids can be added to modulate the pH of the system. A typical formula can contain.

| | |
|---|---|
| Active Ingredients | 0.25–5 g |
| Soluble starch | 80 g |
| Lactose or mannitol | 10 g |
| Magnesium stearate | 1 g |
| Color and flavor | As needed |

Testing the lozenge formulation may be accomplished with regard to their release/dissolution profiles and stability. Stability of rhLF may be monitored by HPLC. The current method uses a Bio-Cad POROS HS (Sulfopropyl based) column. Lactoferrin may be loaded in 100 mM NaPO$_4$ pH 8.0 and eluted with 0–1 N NaCl gradient. It is also possible to perform iron saturation and desaturation studies as well. The stability of the rhLY can be monitored by HPLC and the *Micrococcus luteus* turbidimetric assay. The HPLC profile of the rhLY loads the protein in 5 mM NaPO$_4$ pH 7.4 and elutes with 0.2 M NaCl.

Each lozenge is individually weighed and dissolved in an appropriate volume of purified water to dissolve the active ingredients in the solution to assay for the drug content of the lozenge. Sonication and agitation may be used to aid in the process of drug extraction. The final solution is diluted to the desired final concentration, filtered to remove insoluble excipients and analyzed for the drug concentration using the HPLC methods. The goal is to have a weight variation of less than 10% based on the average value of drug content for both actives.

Another embodiment of the invention uses a chewing gum delivery system. The chewing gum delivery system especially enables sustained contact of the antibacterial agents with the entire oral cavity and therefore, enhances bactericidal and fungicidal efficacy.

Typical formulations for the gum are:

| | |
|---|---|
| Active | 250–1000 mg |
| Crystalline Sorbitol | 910.0 mg |
| Gum Base | 575.0 mg |
| Sorbitol Solution | 500.0 mg |
| Mannitol | 400.0 mg |
| Peppermint Oil | 25.0 mg |
| Spray Dried | 12.5 mg |
| Peppermint | 5.0 mg |
| Grade t Lecithin | 10.0 mg |
| Aspartame | 10.0 mg |
| Sodium Citrate | 10.0 mg |

Yet another embodiment of the present invention contemplates a rapidly dissolving film which can be adhered to the oral cavity thereby releasing a pharmaceutically or cosmetically active agent. The film may contain one or more pharmaceutically active ingredients. Optionally, excipients commonly used to modify the taste of formulations intended for application to the oral cavity. The resulting film is characterized by an instant wettability which causes the film to soften immediately after application to the mucosal tissue thus preventing the patient from experiencing any prolonged adverse feeling in the mouth, and a tensile strength suitable for normal coating, cutting, slitting, and packaging operations.

In another embodiment, a syrup or elixir may contain the active compound, as well as other excipients to enhance flavor, taste, storage, and other pertinent factors. The syrup or elixir may be incorporated into sustained-release preparations and formulations.

In one more embodiment of the invention, the oral formulation may be applied to the teeth, gingival tissues or orthodontic appliance, for slow, long-term sustained release at efficacious levels into the salivary fluids of the oral cavity. In addition the composition of the invention is colorless and visually undetectable by those unaware of the treatment.

Since the efficacy of final formulations is based on delivery of effective concentration of active ingredients for the longest possible duration from each dose, testing to determine a release profile is critical test for the final product. The test can be carried out using test method <711> the United States Pharmnacopoeia. Method 1, where the formulation is enclosed in a the basket rotated at 100 rpm may be used. The dissolution medium may be 1000 mL water maintained at 37° C. Samples are drawn at predetermined time points (e.g. 1,2,4,6,8,10,15 minutes) and the data plotted as amount released as a function of time. The active ingredients may be assayed using standard HPLC methods. Release may be, for example, according to either embodiment in the following table:

| Time (minutes) | Embodiment 1 | Embodiment 2 |
|---|---|---|
| 1 | 0–35% | 0–20% |
| 2 | 10–50% | 5–35% |
| 4 | 25–65% | 15–50% |
| 6 | 40–85% | 25–60% |
| 8 | 60–100% | 40–75% |
| 10 | 80–100% | 60–90% |
| 15 | 95–100% | 80–100% |

The most appropriate release profile is the one that maintains active ingredients at a concentration in the effective range for the longest duration of time. For the purpose of extrapolating the dissolution data to dissolution in buccal cavity, the volume of dissolution medium may be varied down to as low as 100 mL. This test not only provides data to select the desired formulation, but also serves as a quality control test for purposes of reproducing the formulation.

Among the parameters monitored during this test is the time taken for the lozenge to completely disintegrate or dissolve in the dissolution medium. A disintegration time of 10–15 minutes is typically considered an acceptable level of performance. The stability of the lozenges may also be tested. Formulations resulting from the above studies may be prepared in bulk quantities (several hundred units) and divided into several groups. These groups are tested according to the generally accepted accelerated methods of stability testing. The groups are stored at different temperatures (e.g. 25, 35 and 40° C.). At predetermined time intervals (e.g. 1,2,4,8 weeks), the units are removed and tested for the total content of the active ingredients as well as for the release/dissolution profile. In addition, other properties such as the color changes, physical appearance and dose uniformity are observed.

Selection of the final formulation is based on the results of above studies, and 2–3 formulations may be selected for clinical studies, as well as for use as a product for sale. These formulations are selected on the basis of their release profiles and stability. The final candidates bracket the desired profile based on release studies.

In one embodiment of the invention, the lozenge is chewed or let to dissolve for 30 seconds to ten minutes to maximize absorption of the active ingredients through the lining of the oral cavity and their absorption into the blood and lymphatic system.

The dosage may vary based on a number of factors. Further description of possible treatment methods is provided in U.S. Pat. No. 6,066,469 which is incorporated in its entirety by this reference.

Completion of the lozenge formulation and testing will result in availability of test formulations of lozenges for the treatment of oral candidiasis. The next step in the development of the alternative antifungal treatment is the safety and pharmacodynamics study in healthy volunteers, followed by testing in a small population having OPC, finally followed by a larger multi-center testing for use of rhLF and rhLY in a lozenge for treatment and/or prophylaxis of oral candidiasis in immunocompromised and other patients.

All publications, patents and patent applications are herein expressly incorporated by reference in their entirety to the same extent as if each individual publication, patent or patent application was specifically and indicated individually to be incorporated by reference in its entirety.

The following examples illustrate but are not intended in any way to limit the invention.

EXAMPLE 1

In vitro culture is employed to determine the feasibility of using recombinant human lactoferrin (rhLF) and recombinant human lysozyme (rhLY) produced in rice for *Candida* growth inhibition. Studies on the in vitro inhibition of *Candida* reported in the literature have used two different methods. Work using salivary concentrations of lactoferrin and lysozyme is performed by incubation with inhibitory compounds followed by plating on Sabouraud dextrose agar (SDA) and counting of colony-forming units. See Soukka et al., Fungicidal effect of human lactoferrin against *Candida albicans*. FEMS Microbiol Lett. 1992. 69(3): p. 223–8. The NCCLS reference method for broth dilution antifungal susceptibility testing of yeast, M27-A2, was used in studies by Kuipers. See Kuipers et al., Synergistic fungistatic effects of lactoferrin in combination with antifungal drugs against clinical *Candida* isolates. Antimicrob Agents Chemother. 1999. 43(11): p. 2635–41; Kuipers, M. E., et al., Conditions influencing the in vitro antifungal activity of lactoferrin combined with anti-mycotics against clinical isolates of *Candida*. Impact on the development of buccal preparations of lactoferrin. Apmis. 2002. 110(4): p. 290–8; and Kuipers et al., Design and fungicidal activity of mucoadhesive lactoferrin tablets for the treatment of oropharyngeal candidosis. Drug Deliv. 2002. 9(1): p. 31–8.

In order to compare and reconcile the data from different methods, both methods are used initially to study the growth and inhibition of ATCC strains of *Candida albicans* numbers 90028 (NCCLS reference strain), 28366 (Soukka) and 10231(Kuipers). Briefly, in the colony forming unit method the stock inoculum is grown in brain heart infusion broth (BHI) at 37° C. Cells at $2 \times 10^7$ are washed and re-suspended in ice-cold 0.05 mM KCl buffered to pH for testing. Lactoferrin or lysozyme and fungal cell suspension are mixed in buffered KCl and incubated with mixing at 37° C. for 1 hour. After incubation, a 1:50 dilution is plated on SDA, incubated at 37° C. for 24 to 48 hours. Colony forming units are counted at the end of incubation.

In the NCCLS or Kuipers method, yeast cells are grown on SDA at 35° C. Five colonies—1 mm in diameter are selected from a 24 hour culture and suspended in sterile saline. This suspension is then adjusted for yeast density spectrophotometrically and used to prepare a stock inoculum in RPMI 1640 with glutamine, without bicarbonate and with 0.165 mol/L MOPS (3-(N-morpholino) propanesulfonic acid). The NCCLS microdilution method mixes equal volumes of 2× yeast cell suspension and 2× antifungal agent suspension in a 96-well microtiter plate. Growth is monitored by turbidity measurements at times 0, 24 and 48 hours with a BioRad 3550 automated microplate reader at 630 nm. Normal growth curves can be obtained using both methods by testing intermediate time points.

By comparing the two methods (the Soukka and Kuipers methods), if conflicting results occur, it may be possible to determine which method provides data that extrapolate more readily to in vivo conditions.

Using plating and turbidity methods the anti-mycotic activity of rhLF and rhLY is determined. Recombinant hLF levels from 0.01 to 100 mg/mL are tested for inhibition of growth. Testing is done using apo-lactoferrin, holo-lactoferrin and the unmodified recombinant lactoferrin. Final steps in the purification process allow for the saturation or desaturation of the purified lactoferrin. The iron saturation is monitored using $A_{280}/A_{465}$. Since bicarbonate ion is important for the binding of iron to lactoferrin, the effect of addition of bicarbonate to the media is tested as well.

In parallel with the studies on the inhibitory effects of rhLF, similar studies are done using the rhLY. As with the lactoferrin, both culture methods are used for the studies. Since lactoferrin and lysozyme are present in the saliva at similar concentrations, 0.01 to 100 mg/mL of rhLY may be screened for inhibitory effects. Completion of the studies using the individual recombinant proteins will provide concentration ranges for testing of the combined effectiveness of both proteins. The NCCLS microdilution method provides the most convenient method for testing the individual proteins and the combinations using a matrix pattern in the 96-well plate, however, the plating method can also be accommodated if necessary. Using established conditions of pH, iron saturation for lactoferrin, and bicarbonate ion, combination studies will determine the additive or synergistic action of rhLF and rhLY against *Candida*.

Example embodiments of the present invention have now been described in accordance with the above advantages. It will be appreciated that these examples are merely illustrative of the invention. Many variations and modifications will be apparent to those skilled in the art.

What is claimed is:

1. A method of making an anti-infective composition suitable for oral administration comprising an agent including at least one protein selected from the group consisting of lactoferrin protein and lysozyme protein, comprising the steps of:
    a) expressing a nucleic acid encoding at least one protein selected from the group consisting of human lactoferrin protein and human lysozyme protein in a monocot seed;
    b) isolating the at least one protein from the seed, wherein the at least one protein comprises about 3% or greater of the total soluble protein in the seed;
    c) combining the at least one protein with a pharmaceutically acceptable carrier or diluent to provide a composition suitable for oral administration.

2. The method of making the anti-infective composition for oral administration according to claim 1, wherein the composition of the protein for oral administration is a lozenge.

3. The method of making the anti-infective composition for oral administration according to claim 1, wherein the composition of the protein for oral administration is a chewing gum.

4. The method of making the anti-infective composition for oral administration according to claim 1, wherein the composition of the protein for oral administration is a dissolving film.

5. The method of making the anti-infective composition for oral administration according to claim 1, wherein the composition of the protein for oral administration is a suspension.

6. The method of making the anti-infective composition for oral administration according to claim 1, wherein the composition of the protein for oral administration is a solution.

7. The method of making the anti-infective composition for oral administration according to claim 1, further comprising administering the protein on epithelial surfaces of the oral cavity.

8. The method of making the anti-infective composition for oral administration according to claim 1, wherein the at least one protein comprises about >5% or greater of the total soluble protein in the seed.

9. The method of making the anti-infective composition for oral administration according to claim 1, wherein the at least one protein comprises about >10% or greater of the total soluble protein in the seed.

10. The method of making the anti-infective composition for oral administration according to claim 1, wherein the at least one protein comprises about >15% or greater of the total soluble protein in the seed.

11. The method of making the anti-infective composition for oral administration according to claim 1, wherein the at least one protein comprises about >20% or greater of the total soluble protein in the seed.

* * * * *